United States Patent
Chen et al.

(10) Patent No.: US 9,587,274 B2
(45) Date of Patent: Mar. 7, 2017

(54) SYSTEM AND METHOD FOR CORRECTING PRIMER EXTENSION ERRORS IN NUCLEIC ACID SEQUENCE DATA

(75) Inventors: Yi-Ju Chen, New Haven, CT (US);
Keith McDade, Higganum, CT (US);
John Simpson, Madison, CT (US)

(73) Assignee: 454 Life Sciences Corporation, Branford, CT (US)

( * ) Notice: Subject to any disclaimer, the term of this patent is extended or adjusted under 35 U.S.C. 154(b) by 805 days.

(21) Appl. No.: 13/608,841

(22) Filed: Sep. 10, 2012

(65) Prior Publication Data

US 2013/0054171 A1    Feb. 28, 2013

Related U.S. Application Data

(63) Continuation of application No. 12/224,065, filed as application No. PCT/US2007/004187 on Feb. 15, 2007, now Pat. No. 8,301,394.

(60) Provisional application No. 60/774,354, filed on Feb. 16, 2006.

(51) Int. Cl.
| | |
|---|---|
| G06F 19/20 | (2011.01) |
| G06F 15/00 | (2006.01) |
| C12Q 1/68 | (2006.01) |
| G06F 19/24 | (2011.01) |
| G06F 19/22 | (2011.01) |

(52) U.S. Cl.
CPC ......... *C12Q 1/6848* (2013.01); *C12Q 1/6869* (2013.01); *G06F 19/24* (2013.01); *G06F 19/22* (2013.01)

(58) Field of Classification Search
None
See application file for complete search history.

(56) References Cited

U.S. PATENT DOCUMENTS

| | | |
|---|---|---|
| 6,210,891 B1 | 4/2001 | Nyren et al. |
| 6,258,568 B1 | 7/2001 | Nyren |
| 6,274,320 B1 | 8/2001 | Rothberg et al. |
| 6,828,100 B1 | 12/2004 | Ronaghi |
| 6,911,327 B2 | 6/2005 | McMillan et al. |
| 7,133,782 B2 | 11/2006 | Odedra |
| 7,211,390 B2 | 5/2007 | Rothberg et al. |
| 7,244,559 B2 | 7/2007 | Rothberg et al. |
| 7,264,929 B2 | 9/2007 | Rothberg et al. |
| 7,323,305 B2 | 1/2008 | Leamon et al. |

(Continued)

FOREIGN PATENT DOCUMENTS

| | | |
|---|---|---|
| WO | WO-2005040425 A2 | 5/2005 |
| WO | WO-2007098049 A2 | 8/2007 |

OTHER PUBLICATIONS

Ahmadian et al. "Pyrosequencing: History, Biochemistry and Future." *Clin. Chim. Acta.* 363(2006):83-94.

(Continued)

*Primary Examiner* — John S Brusca
(74) *Attorney, Agent, or Firm* — Cooley LLP; Ivor R. Elrifi; Christina K. Stock

(57) ABSTRACT

An embodiment of method for correcting an error associated with phasic synchrony of sequence data generated from a population of substantially identical copies of a template molecule is described that comprises (a) detecting a signal generated in response to an incorporation of one or more nucleotides in a sequencing reaction; (b) generating a value for the signal; and (c) correcting the value for the phasic synchrony error using a first parameter and a second carry forward parameter.

22 Claims, 9 Drawing Sheets

(56) References Cited

U.S. PATENT DOCUMENTS

| | | | |
|---|---|---|---|
| 7,335,762 | B2 | 2/2008 | Rothberg et al. |
| 2003/0219797 | A1 | 11/2003 | Zhao et al. |
| 2004/0197845 | A1 | 10/2004 | Hassibi et al. |
| 2006/0040297 | A1 | 2/2006 | Leamon et al. |
| 2007/0092872 | A1 | 4/2007 | Rothberg et al. |
| 2007/0281300 | A1 | 12/2007 | Russell et al. |
| 2009/0176200 | A1 | 7/2009 | Wakita et al. |

OTHER PUBLICATIONS

Baldi et al. "Machine Learning Foundations: The Probabilistic Network." *Bioinformatics: The Machine Learning Approach*. Cambridge, MA: MIT Press. (2000):39-557.
Brockman et al. "Quality Scores and SNP Detection in Sequencing-by-Synthesis Systems." *Genome Res.* 18(2008):763-770.
International Search Report issued in International Application No. PCT/US2007/04187, mailed Jun. 16, 2008.
International Search Report issued in International Application No. PCT?EP2011/054817, mailed Jun. 16, 2011.
Langaee et al. "Genetic Variation Analyses by Pyrosequencing." *Mutat. Res.* 573(2005):96-102.
Margulies et al. "Genome Sequencipkg in Microfabriated High-Density Picolitre Reactors." *Nature*. 437.(2005):376-380, pp. 376-380.
Margulies et al. "Supplementary Methods for the Article 'Genome Sequencing in Microfabricated High-Density Picolitre Reactors.'" *Nature*. 437.(2005):1-34, pp. 376-380.
Metzker. "Emerging Technologies in DNA Sequencing." *Genome Res.* 15(2005):1767-1776.
Office Action issued in Japanese Application No. 2008-555390 mailed May 11, 2012. (English Translation).
Ronaghi. "Pyrosequencing Sheds Light on DNA Sequencing." *Genome Res.* 11(2001):3-11.
Supplementary Search Report issued in European Application No. 07750981, mailed Apr. 22, 2009.
Communication issued in European Application No. 07750981.8, dated Mar. 11, 2013.
Communication pursuant to Article 94(3) EPC issued in European Application No. 07750981.8 dated Dec. 10, 2010.
Extended European Search Report issued in European Application No. 07750981.8 dated May 4, 2009.
Office Action issued in Chinese Application No. 200780005575.0 dated Jan. 29, 2010. (English Translation and Chinese Original).
Office Action issued in Chinese Application No. 200780005575.0 dated May 13, 2011. (English Translation and Chinese Original).
Office Action issued in Canadian Application No. 2,637,617 dated Jul. 24, 2013.
Extended European Search Report issued in European Application No. 12196383.9, mailed Mar. 7, 2013.
Office Action issued in Japanese Application No. 2008-555390, dated Jan. 21, 2013. (Japanese Original and English Abstract).
Margulies et al. "Supplementary Figures for the Article' Genome Sequencing in Microfabricated High-Density Picolitre Reactors:" Nature, 437.7057 (2005): 1-12.
Margulies et al. "Supplementary Tables for the Article 'Genome Sequencing in Microfabricated High-Density Picolitre Reactors:" Nature, 437.7057 (2005): 1-6.

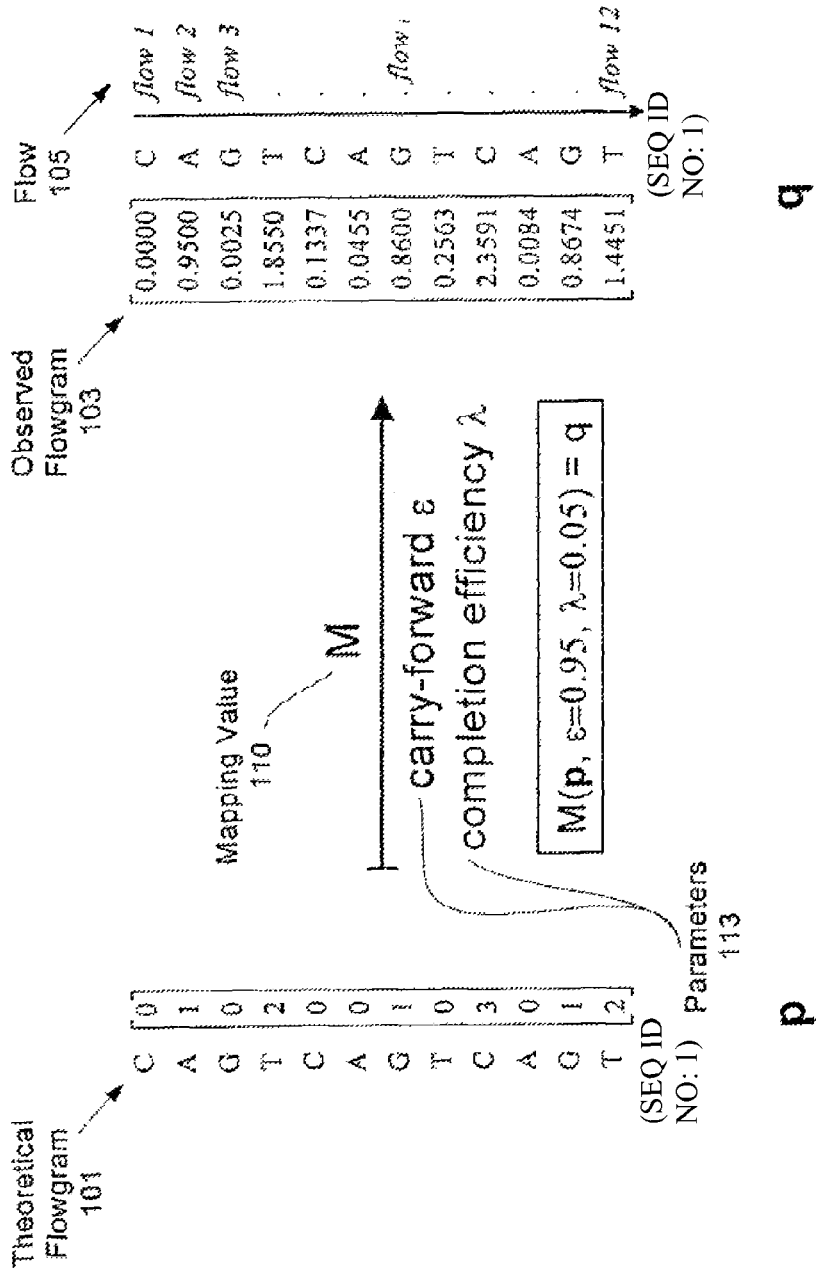

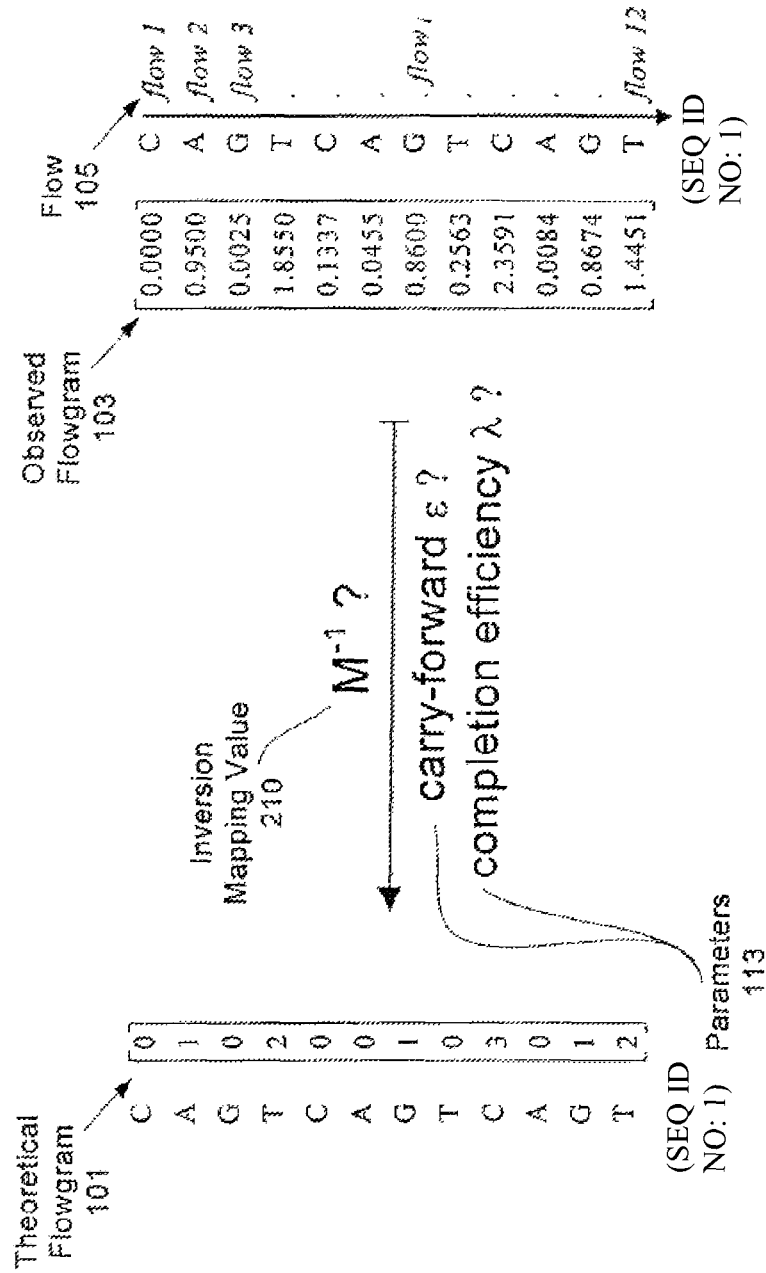

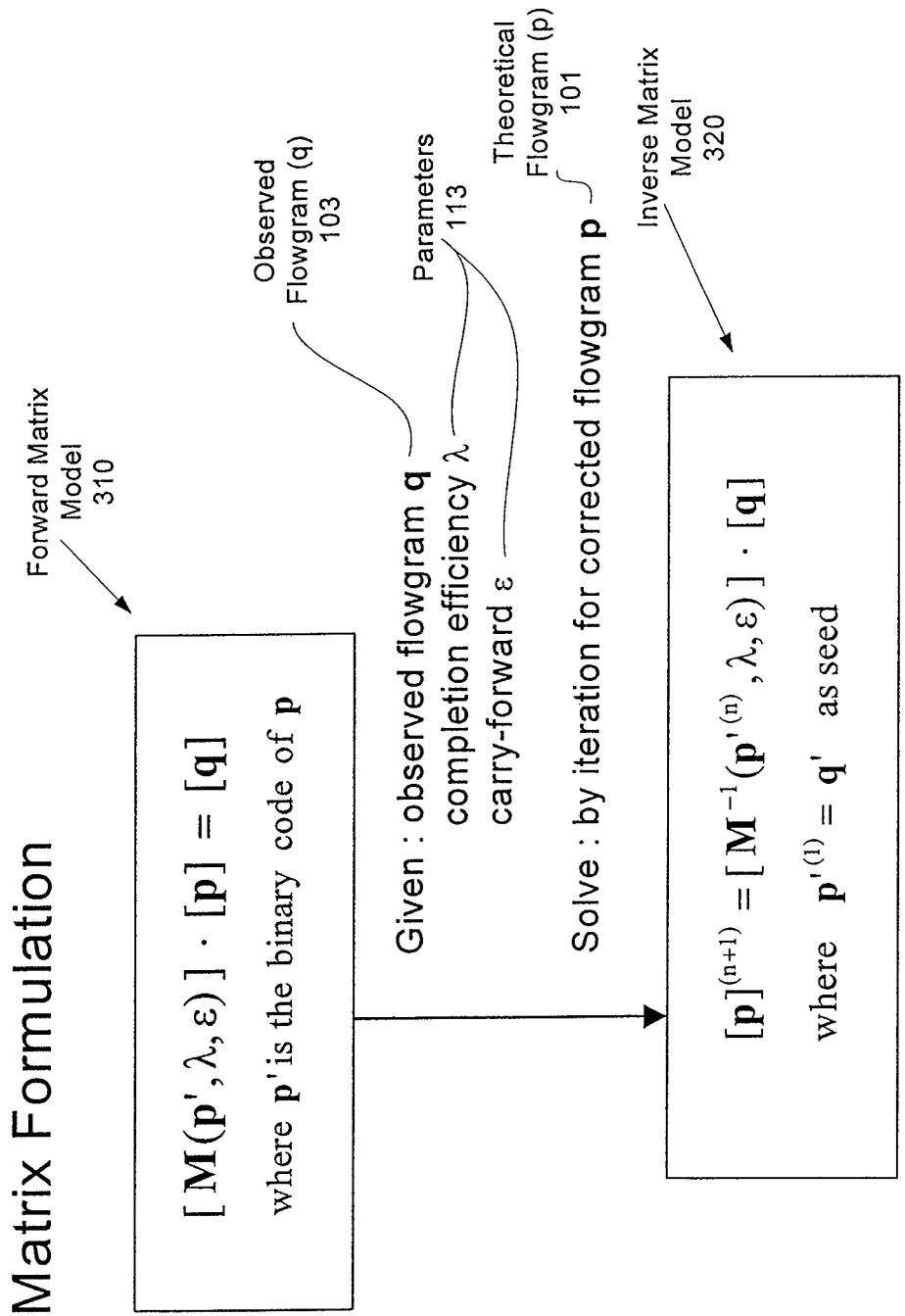

CAFIE Forward

Figure 3B $$[M(p', \lambda=0.95, \varepsilon=0.05)] \quad [p] = [q] \quad \text{Forward Matrix Model 310}$$

| | | | | | | | | | | | | [p] | [q] | Flow 105 | |
|---|---|---|---|---|---|---|---|---|---|---|---|---|---|---|---|
| 0 | 0 | 0 | 0 | 0 | 0 | 0 | 0 | 0 | 0 | 0 | 0 | 0 | 0.0000 | C | flow 1 |
| 0.95 | 0 | 0 | 0 | 0 | 0 | 0 | 0 | 0 | 0 | 0 | 0 | 1 | 0.9500 | A | flow 2 |
| 0.0025 | 0 | 0 | 0 | 0 | 0 | 0 | 0 | 0 | 0 | 0 | 0 | 0 | 0.0025 | G | flow 3 |
| 0 | 0 | 0.9049 | 0 | 0 | 0 | 0 | 0 | 0 | 0 | 0 | 0 | 2 | 1.8550 | T | . |
| 0 | 0 | 0.0024 | 0 | 0.0452 | 0 | 0 | 0 | 0 | 0 | 0 | 0 | 0 | 0.1337 | C | . |
| 0.0451 | 0 | 0 | 0 | 0 | 0 | 0.0430 | 0 | 0 | 0 | 0 | 0 | 0 | 0.0455 | A | . |
| 0.0001 | 0 | 0.0860 | 0 | 0.8189 | 0 | 0 | 0 | 0 | 0 | 0 | 0 | 1 | 0.8600 | G | . flow$_i$ |
| 0 | 0 | 0.0002 | 0 | 0.0065 | 0 | 0.0001 | 0 | 0.0409 | 0 | 0.0389 | 0 | 0 | 0.2563 | T | . |
| 0.0021 | 0 | 0 | 0 | 0 | 0 | 0.7861 | 0 | 0.0001 | 0 | 0.0001 | 0 | 3 | 2.3591 | C | . |
| 0 | 0 | 0 | 0 | 0 | 0 | 0.0021 | 0 | 0 | 0 | 0 | 0 | 0 | 0.0084 | A | . |
| 0 | 0 | 0 | 0 | 0.1167 | 0 | 0 | 0 | 0.7507 | 0 | 0 | 0 | 1 | 0.8674 | G | . |
| 0 | 0 | 0.0061 | 0 | 0.0006 | 0 | 0 | 0 | 0.0020 | 0 | 0.7151 | 0 | 2 | 1.4451 | T | flow 12 |

Figure 4A

CAFIE Inversion $[\mathbf{p}]^{(2)} = [\mathbf{M}(\mathbf{p'}^{(1)}, \lambda = 0.95, \varepsilon = 0.05)]^{-1} \cdot [\mathbf{q}]$ Inverse Matrix Model 320

$$[\mathbf{p}]^{(2)} = \begin{bmatrix} 0 \\ 1.0502 \\ -0.0000 \\ 0.0000 \\ 0.0000 \\ 0.0000 \\ -0.0002 \\ 0 \\ -0.0000 \\ 0 \\ 0.0000 \\ 0.0000 \end{bmatrix} \begin{bmatrix} 0 & 0 & 0 & 0 & 0 & 0 & 0 & 0 & 0 & 0 & 0 \\ 0.0028 & 0.0000 & 0.0000 & 0 & 0.0499 & 0 & 0 & 0 & 0 & 0 & 0 \\ -0.0000 & 0.0000 & -0.0000 & -0.0000 & -0.0000 & 0.0000 & -0.0000 & 0.0024 & -0.0000 & 0.0000 & 0 \\ 0.0000 & 1.0954 & 0.0029 & -0.0000 & -0.0000 & -0.0618 & 0.1032 & -0.0000 & 0.0034 & -0.0056 & 0 \\ 0.0000 & -0.0000 & -0.0000 & -0.0000 & -0.0000 & -0.0000 & -0.0000 & -0.0000 & 0.0000 & 0.0000 & 0 \\ 0.0000 & 0.0000 & -0.0000 & 0.0000 & -0.0000 & -0.0000 & -0.0000 & -0.0000 & 0.0000 & -0.0000 & 0 \\ -0.0000 & -0.0003 & -0.0002 & 0.0000 & -0.0000 & 1.2307 & 0.0032 & -0.0000 & -0.0671 & -0.0002 & 0 \\ 0 & 0 & 0 & 0.0002 & 0 & 0 & 0 & 1.2682 & 0 & 0 & 0 \\ -0.0000 & -0.0005 & 0.0693 & 0.0000 & -0.0000 & 0.0000 & -0.0001 & 0.0000 & -0.0000 & -0.0002 & 0 \\ 0 & 0 & 0 & -0.0000 & 0 & 0 & 0 & 0.0033 & 0 & 0 & 0 \\ 0.0000 & 0.0001 & 0.0000 & 0.0000 & -0.0000 & -0.1913 & -0.0007 & 0.0000 & 1.3424 & 0.0000 & 0 \\ 0.0000 & -0.0165 & -0.0001 & -0.0000 & 0.0000 & -0.0002 & 0.0743 & -0.0000 & -0.0037 & 1.3943 \end{bmatrix} \begin{bmatrix} 0.0000 \\ 0.9500 \\ 0.0025 \\ 1.8550 \\ 0.1337 \\ 0.0455 \\ 0.8600 \\ 0.2563 \\ 2.3591 \\ 0.0084 \\ 0.8674 \\ 1.4451 \end{bmatrix} \begin{matrix} \leftarrow flow\ 1 \\ \leftarrow flow\ 2 \\ \leftarrow flow\ 3 \\ \cdot \\ \cdot \\ \leftarrow flow_i \\ \cdot \\ \cdot \\ \leftarrow flow\ 12 \end{matrix}$$

Flow 105

$=\begin{bmatrix} 0 \\ 1 \\ 0 \\ 2 \\ 0 \\ 0 \\ 1 \\ 0 \\ 3 \\ 0 \\ 1 \\ 2 \end{bmatrix}$

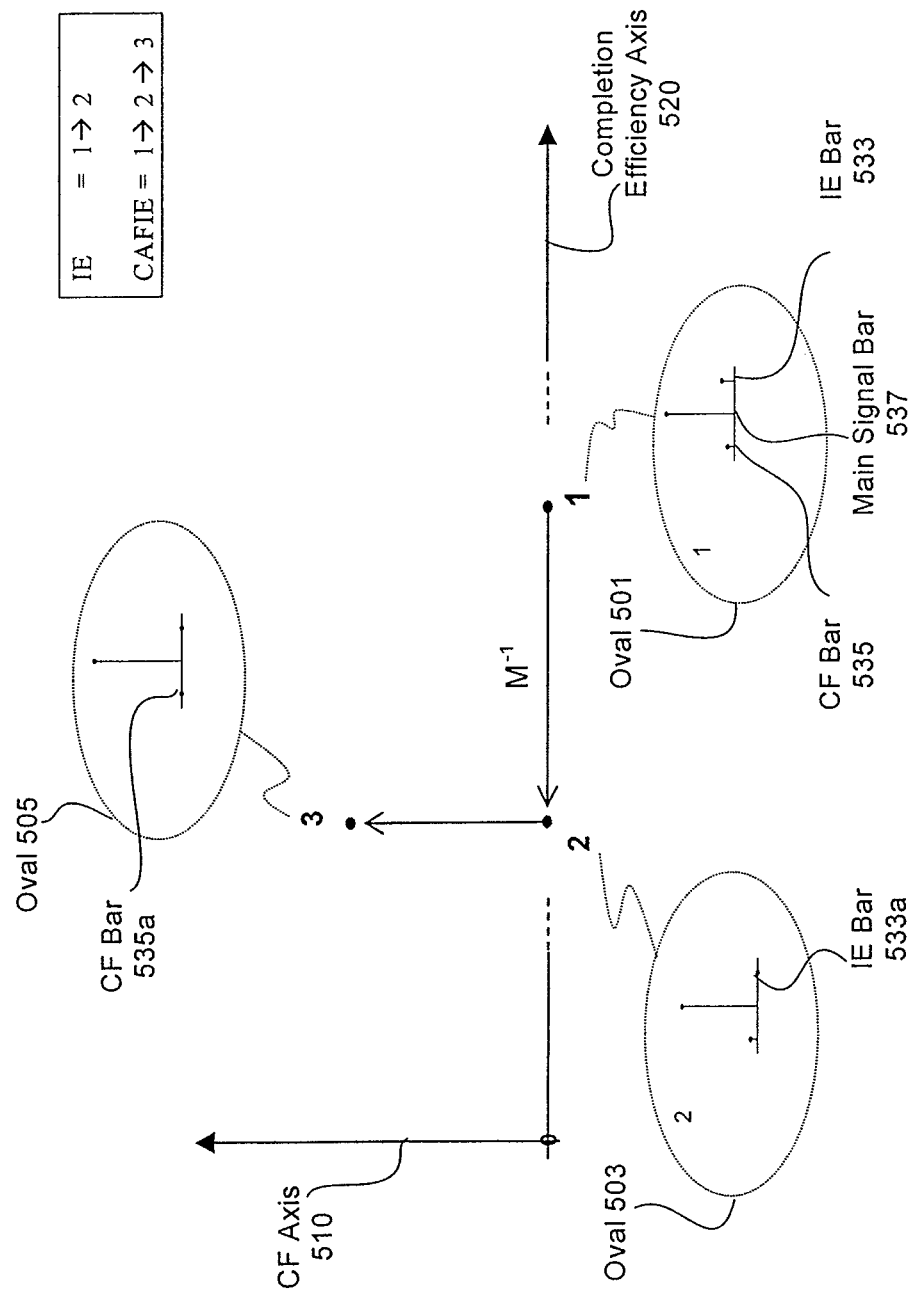

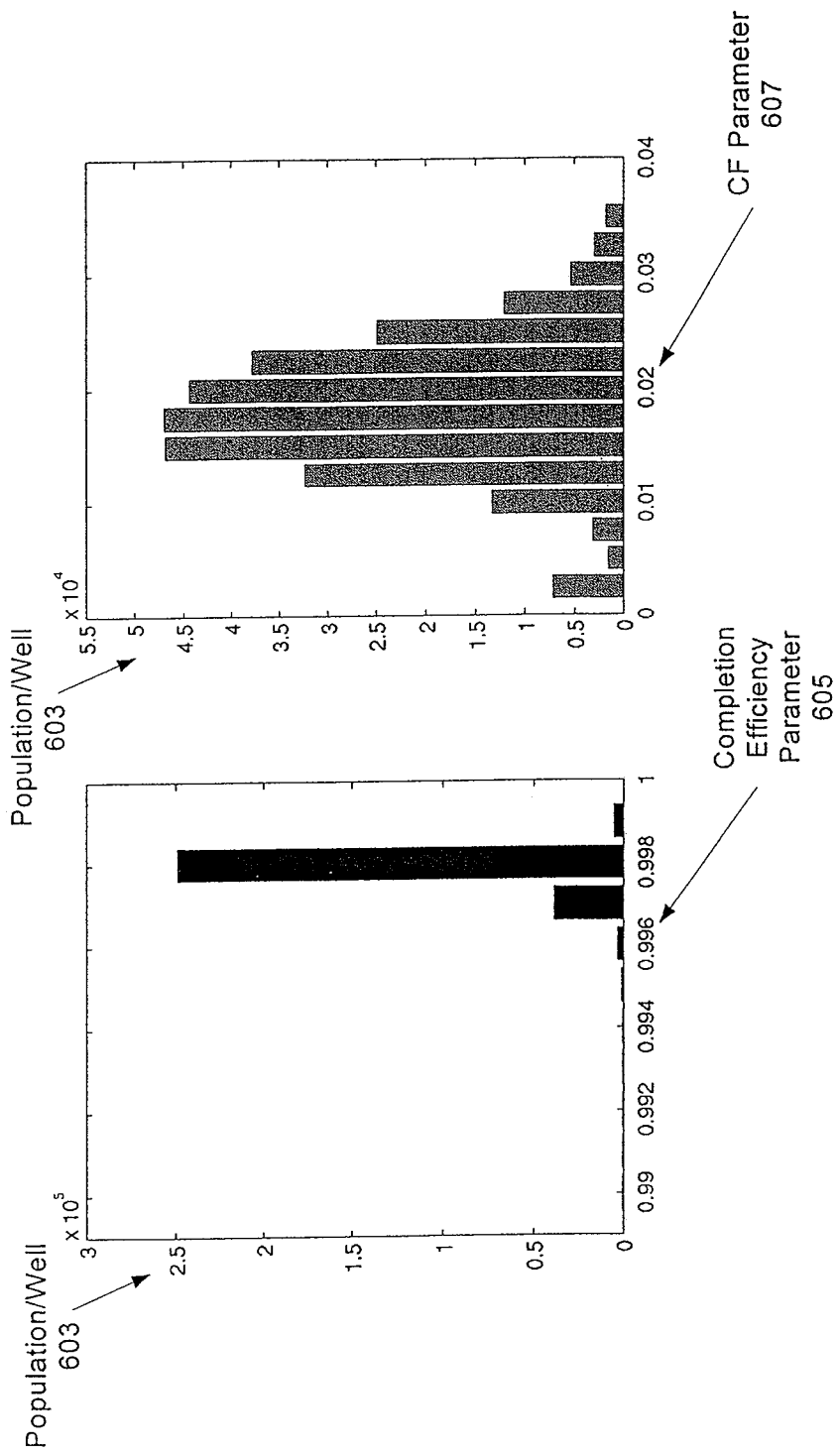

SEQUENCE LISTING

<160> NUMBER OF SEQ ID NOS: 1

<210> SEQ ID NO 1
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 1
cagtcagtca gt                                                                12

SYSTEM AND METHOD FOR CORRECTING PRIMER EXTENSION ERRORS IN NUCLEIC ACID SEQUENCE DATA

RELATED APPLICATIONS

The present application is continuation of U.S. application Ser. No. 12/224,065, which is a National Stage of International Application No. PCT/US2007/004187, filed on Feb. 15, 2007, which claims priority to U.S. Provisional Patent Application Ser. No. 60/774,354, filed on Feb. 16, 2006. The contents of all of these applications are expressly incorporated herein by reference in their entireties.

INCORPORATION-BY-REFERENCE OF SEQUENCE LISTING

The contents of the file named "454L-28C01US_ST25.txt," which was created on Oct. 19, 2015 and is 1 KB in size, are hereby incorporated by reference in their entirety.

REFERENCE TO COMPUTER PROGRAM LISTING APPENDIX

This application includes a computer program listing appendix entitled "Appendix1.txt", created on Oct. 19, 2015, and having a size of 38 KB, which was electronically filed with this patent document. The Appendix1.txt file is hereby incorporated by reference.

FIELD OF THE INVENTION

The present invention relates to the field of molecular biology. More specifically, the invention relates to correcting errors in nucleic acid sequence data generated by what are generally referred to as "Sequencing-by-Synthesis" (SBS) techniques.

BACKGROUND OF THE INVENTION

Sequencing-by-synthesis (SBS) generally refers to methods for determining the identity or sequence composition of one or more nucleotides in a nucleic acid sample, wherein the methods comprise the stepwise synthesis of a single strand of polynucleotide molecule complementary to a template nucleic acid molecule whose nucleotide sequence composition is to be determined. For example, SBS techniques typically operate by adding a single nucleic acid (also referred to as a nucleotide) species to a nascent polynucleotide molecule complementary to a nucleic acid species of a template molecule at a corresponding sequence position. The addition of the nucleic acid species to the nascent molecule is generally detected using a variety of methods known in the art that include, but are not limited to what are referred to as pyrosequencing or fluorescent detection methods such as those that employ reversible terminators. Typically, the process is iterative until a complete (i.e. all sequence positions are represented) or desired sequence length complementary to the template is synthesized. Some examples of SBS techniques are described in U.S. Pat. No. 6,274,320, which is hereby incorporated by reference herein in its entirety for all purposes; and U.S. patent application Ser. Nos. 10/788,529; 09/814,338; 10/299,180; 10/222,298; 10/222,592, each of which is hereby incorporated by reference herein in its entirety for all purposes.

In some embodiments of SBS, an oligonucleotide primer is designed to anneal to a predetermined, complementary position of the sample template molecule. The primer/template complex is presented with a nucleotide specie in the presence of a nucleic acid polymerase enzyme. If the nucleotide specie is complementary to the nucleic acid specie corresponding to a sequence position on the sample template molecule that is directly adjacent to the 3' end of the oligonucleotide primer, then the polymerase will extend the primer with the nucleotide specie. Alternatively, in some embodiments the primer/template complex is presented with a plurality of nucleotide species of interest (typically A, G, C, and T) at once, and the nucleotide specie that is complementary at the corresponding sequence position on the sample template molecule directly adjacent to the 3' end of the oligonucleotide primer is incorporated. In either of the described embodiments, the nucleotide species may be chemically blocked (such as at the 3'-O position) to prevent further extension, and need to be deblocked prior to the next round of synthesis. As described above, incorporation of the nucleotide specie can be detected by a variety of methods known in the art, e.g. by detecting the release of pyrophosphate (PPi) (examples described in U.S. Pat. Nos. 6,210,891; 6,258,568; and 6,828,100, each of which is hereby incorporated by reference herein in its entirety for all purposes), or via detectable labels bound to the nucleotides. Some examples of detectable labels include but are not limited to mass tags and fluorescent or chemiluminescent labels. In typical embodiments, unincorporated nucleotides are removed, for example by washing. In the embodiments where detectable labels are used, they will typically have to be inactivated (e.g. by chemical cleavage or photobleaching) prior to the following cycle of synthesis. The next sequence position in the template/polymerase complex can then be queried with another nucleotide species, or a plurality of nucleotide species of interest, as described above. Repeated cycles of nucleotide addition, primer extension, signal acquisition, and washing result in a determination of the nucleotide sequence of the template strand.

In typical embodiments of SBS, a large number or population of substantially identical template molecules (e.g. $10^3$, $10^4$, $10^5$, $10^6$ or $10^7$ molecules) are analyzed simultaneously in any one sequencing reaction, in order to achieve a signal which is strong enough for reliable detection. What is referred to as "homogeneous extension" of nascent molecules associated with substantially all template molecules in a population of a given reaction is required for low signal-to-noise ratios. The term "homogeneous extension", as used herein, generally refers to the relationship or phase of the extension reaction where each of the substantially identical template molecules described above are homogenously performing the same step in the reaction. For example, each extension reaction associated with the population of template molecules may be described as being in phase or in phasic synchrony with each other when they are performing the same reaction step at the same sequence position for each of the associated template molecules.

However those of ordinary skill in the related art will appreciate that a small fraction of template molecules in each population loses or falls out of phasic synchronism with the rest of the template molecules in the population (that is, the reactions associated with the fraction of template molecules either get ahead of, or fall behind, the other template molecules in the sequencing reaction run on the population (some examples are described in Ronaghi, M. Pyrosequencing sheds light on DNA sequencing. Genome Res. 11, 3-11 (2001), which is hereby incorporated by reference herein in its entirety for all purposes). For example, the failure of the reaction to properly incorporate of one or more nucleotide species into one or more nascent molecules for extension of the sequence by one position results in each subsequent reaction being at a sequence position that is behind and out of phase with the sequence position of the rest of the population. This effect is referred to herein as "incomplete extension" (IE). Alternatively, the improper extension of a nascent molecule by incorporation of one or more nucleotide species in a sequence position that is ahead and out of phase with the sequence position of the rest of the population is referred to herein as "carry forward" (CF). The combined effects of CF and IE are referred to herein as CAFIE.

With respect to the problem of incomplete extension, there may be several possible mechanisms that contribute to IE that may occur alone or in some combination. One example of a possible mechanism that contributes to IE may include a lack of a nucleotide species being presented to a subset of template/polymerase complexes. Another example of a possible mechanism that contributes to IE may include a failure of a subset of polymerase molecules to incorporate a nucleotide species which is properly presented for incorporation into a nascent molecule. A further example of a possible mechanism that contributes to IE may include the absence of polymerase activity at template/polymerase complexes.

An example of yet another mechanism that can account, at least in part, for IE errors in SBS methods may include what is referred to as cyclic reversible termination (CRT) as reviewed by Metzger (Genome Res. 2005 December; 15(12):1767-76, which is hereby incorporated by reference herein in its entirety for all purposes). In CRT, nucleotide species have a modified 3'-O group (commonly referred to as a cap, protecting group, or terminator) which prevents further extension of the nascent molecule after incorporation of single nucleotide species. These protecting groups are designed to be removable by one of a variety of methods including chemical treatment or light treatment. Upon deprotection of the 3'-O position (and creation of a 3'-OH group), the nascent molecule can be extended by another nucleotide specie. However, phasic asynchronism will occur when a fraction of nascent molecules remain protected due to imperfect deprotection efficiency (incomplete deprotection). In the subsequent cycle, this fraction of nascent molecules, remaining protected, will not be extended, and will thus fall behind and out of phase with the sequence position of the rest of the population. However, subsequent deprotection steps may successfully remove at least some of the protecting groups which had previously improperly remained, causing extension to resume, and creating signals from nascent molecules and continue to be out of phasic synchrony with the rest of the population. Those of ordinary skill in the art will appreciate that other factors that contribute to IE may exist and thus are not limited to the examples provided above.

The systems and methods of the presently described embodiments of the invention are directed to the correction IE errors that may arise from any such single or combined causes or mechanisms. For instance, the correction of IE errors caused by a coupling of incomplete deprotection and subsequent successful deprotection is one object of the present invention.

With respect to the problem of CF, there may be several possible mechanisms that contribute to CF that may occur alone or in some combination. For example, one possible mechanism may include excess nucleotide species remaining from a previous cycle. This can occur because the washing protocol performed at the end of a cycle will remove the vast majority, but not necessarily all, of the nucleotide species from the cycle. In the present example a result could include a small fraction of an "A" nucleotide species present in a "G" nucleotide species cycle, leading to extension of a small fraction of the nascent molecule if a complementary "T" nucleotide species is present at the corresponding sequence position in the template molecule. Another example of a possible mechanism causing a carry forward effect may include polymerase error, such as the improper incorporation of a nucleotide species into the nascent molecule that is not complementary to the nucleotide species on the template molecule.

An example of yet another mechanism that can account, at least in part, for CF in SBS methods include cyclic reversible termination (CRT) as reviewed by Metzger (Genome Res. 2005 December; 15(12):1767-76, incorporated by reference above). In the present example, as described above with respect to IE a preparation of 3'-O protected nucleotide species may be employed where some fraction of the nucleotide molecules will lack a protecting group, or have lost the protecting group. Loss of the protecting group may also occur during the sequencing process prior to the intended deprotecting step. Any such lack of a deprotecting group will cause some nascent molecules to be extended by more than one nucleotide species at a time. Such improper multiple extension of a fraction of nascent molecules cause them to move ahead in sequence position and out of phase with the sequence position of the rest of the population. Thus, unprotected nucleotides, and/or prematurely deprotected nucleotides, may contribute, at least in part, to CF in SBS methods involving CRT.

The systems and methods of the presently described embodiments of the invention are directed to the correction of CF errors that may arise from any such single or combined causes or mechanisms. For example, the correction of CF errors that arise due to a lack of protecting groups is one object of the present invention.

Further, the systems and methods of the presently described embodiments of the invention are directed to the correction of both IE errors and CF errors, wherein both types of errors may occur in some combination for a population in the same sequencing reaction. For example, IE and CF may each arise from single or combined causes or mechanisms as described above.

Those of ordinary skill will appreciate that a potential for both IE and CF errors may occur at each sequence position during an extension reaction and thus may have cumulative effects evident in the resulting sequence data. For example, the effects may become especially noticeable towards the end of a series of sequencing reactions, which is also sometimes referred to as a "run" or "sequencing run". Further, IE and CF effects may impose an upper limit to the length of a template molecule that may be reliably sequenced (sometimes referred to as the "read length") using SBS approaches, because the quality of the sequence data decreases as the read length increases.

For example, one method of SBS may generate sequence data comprising over 25 million sequence positions in a typical run with what is referred to as a "Phred" quality score of 20 or better (a Phred quality score of 20 infers that the sequence data is predicted to have an accuracy of 99% or higher). While the overall sequencing throughput with Phred 20 quality for the SBS method is significantly higher than that of sequence data generated by what is known to those in the art as Sanger sequencing methods that employ a capillary electrophoresis technique, it is currently at the cost of substantially shorter read lengths for the SBS method (Margulies et al., 2005, *Nature* 437: 376-80, which is hereby incorporated by reference herein in its entirety for all purpose). Thus increasing the upper limit of the read lengths by avoiding or correcting for degradation of the sequence data produced by IE and CF errors would result in an increase in the overall sequencing throughput for SBS methods.

Therefore, it is desirable to provide systems and methods directed to correcting for IE and/or CF errors in sequence data produced by sequencing-by-synthesis methods of nucleic acid sequencing.

A number of references are cited herein, the entire disclosures of which are incorporated herein, in their entirety, by reference for all purposes. Further, none of these references, regardless of how characterized above, is admitted as prior art to the invention of the subject matter claimed herein.

SUMMARY OF THE INVENTION

Embodiments of the invention relate to the determination of the sequence of nucleic acids. More particularly, embodiments of the invention relate to methods and systems for correcting errors in data obtained during the sequencing of nucleic acids by SBS.

An embodiment of method for correcting an error associated with phasic synchrony of sequence data generated from a population of substantially identical copies of a template molecule is described that comprises (a) detecting a signal generated in response to an incorporation of one or more nucleotides in a sequencing reaction; (b) generating a value for the signal; and (c) correcting the value for the phasic synchrony error using a first parameter and a second parameter.

In some implementations, steps (a)-(c) may be repeated for each sequence position of a template molecule, and each corrected value may be incorporated into a representation of the template molecule that may include a flowgram representation.

Also, an embodiment of a method for correcting an error associated with phasic synchrony of sequence data generated from a population of substantially identical copies of a template molecule is described that comprises (a) detecting a signal generated in response to an incorporation of one or more nucleotides in a sequencing reaction; (b) generating a value for the signal; (c) incorporating the value into a representation associated with a sequence of a template molecule; (d) repeating steps (a)-(c) for each sequence position of the template molecule; (e) correcting each value for the phasic synchrony error in the representation using a first parameter and a second parameter; and (f) generating a corrected representation using the corrected values.

Further, an embodiment of a method for correcting an error associated with phasic synchrony of sequence data generated from a population of substantially identical copies of a template molecule is described that comprises (a) detecting a signal generated in response to an incorporation of one or more nucleotides in a sequencing reaction; (b) generating a value for the signal; (c) incorporating the value into a representation associated with a sequence of a template molecule; (d) repeating steps (a)-(c) for each sequence position of the template molecule; (e) dividing the representation into a plurality of sub-sets, wherein each sub-set comprises one or more sequence positions of the template molecule; (f) estimating the synchrony error for a first parameter and a second parameter in each sub-set; (g) correcting each value in each sub-set for the phasic synchrony error using the synchrony error estimations for the first parameter and for the second parameter for each respective sub-set; and (h) combining the corrected sub-sets into a corrected representation using the corrected values.

Additionally, an embodiment of a system for correcting an error associated with phasic synchrony of sequence data generated from a population of substantially identical copies of a template molecule is described that comprises a computer with program code stored for execution thereon that performs a method that comprises (a) generating a value for a signal detected in response to an incorporation of one or more nucleotides in a sequencing reaction; and (b) correcting the value for the phasic synchrony error using a first parameter and a second parameter.

Even further, an embodiment of a system for correcting error associated with phasic synchrony of sequence data generated from a population of substantially identical copies of a template molecule is described that comprises a computer with program code stored for execution thereon that performs a method that comprises (a) generating a value for a signal detected in response to an incorporation of one or more nucleotides in a sequencing reaction; (b) incorporating the value into a representation associated with a sequence of a template molecule; (c) repeating steps (a)-(b) for each sequence position of the template molecule; (d) correcting each value for the phasic synchrony error in the representation using a first parameter and a second parameter; and (e) generating a corrected representation using the corrected values Also, an embodiment of a system for correcting an error associated with phasic synchrony of sequence data generated from a population of substantially identical copies of a template molecule is described that comprises a computer comprising program code stored for execution thereon, the program code performing a method comprising: (a) generating a value for a signal detected in response to an incorporation of one or more nucleotides in a sequencing reaction; (b) incorporating the value into a representation associated with a sequence of a template molecule; (c) repeating steps (a)-(c) for each sequence position of the template molecule; (d) dividing the representation into a plurality of sub-sets, wherein each sub-set comprises one or more sequence positions of the template molecule; (e) estimating the synchrony error for a first parameter and a second parameter in each sub-set; (f) correcting each value in each sub-set for the phasic synchrony error using the synchrony error estimations for the first parameter and for the second parameter for each respective sub-set; and (g) combining the corrected sub-sets into a corrected representation using the corrected values.

The advantages achieved by embodiments of the present invention include but are not limited to: (a) the quality of the sequence data is increased, resulting in lesser depth of sequence coverage being required to achieve a desired level of accuracy of the consensus sequence; b) the useful sequence read length is extended, which means that more high-quality sequence data can be obtained from a single run; (c) because the useful sequence read length is extended, fewer runs will be needed to achieve a given depth of sequence coverage; (d) because the useful sequence read length is extended, fewer sequences are needed to assemble a sequence contig spanning a given region; and (e) the resulting increased read lengths facilitate the assembly of overlapping reads, particularly in repetitive sequence regions.

BRIEF DESCRIPTION OF THE DRAWINGS

The above and further features will be more clearly appreciated from the following detailed description when taken in conjunction with the accompanying drawings. In the drawings, like reference numerals indicate like structures, elements, or method steps and the leftmost digit of a reference numeral indicates the number of the figure in which the references element first appears (for example, element 160 appears first in FIG. 1). All of these conventions, however, are intended to be typical or illustrative, rather than limiting.

FIG. 1 is a simplified graphical representation of one embodiment of a mathematical model for converting a "perfect" theoretical flowgram to a "dirty" observed flowgram;

FIG. 2 is a simplified graphical representation of one embodiment of an inversion of the mapping model of FIG. 1;

FIG. 3a is a simplified graphical representation of one embodiment of models for forward and inverse matrix calculations that include the mapping models of FIGS. 1 and 2;

FIG. 3b is a simplified graphical representation of one embodiment of a forward matrix calculation using the forward model of FIG. 3a;

FIG. 4a is a simplified graphical representation of one embodiment of an inverse matrix calculation using the inverse model of FIG. 3a;

FIG. 4b is a simplified graphical representation of one embodiment of results obtained using different levels of iterative correction using the inverse model of FIGS. 3a and 4a;

FIG. 5 is a simplified graphical representation of one embodiment of results of the CAFIE error correction method of the presently described invention;

FIG. 6 is a simplified graphical representation of one embodiment of the distribution of parameter values across a sample of populations of substantially identical template molecules.

DETAILED DESCRIPTION OF THE INVENTION

Figure 4B:
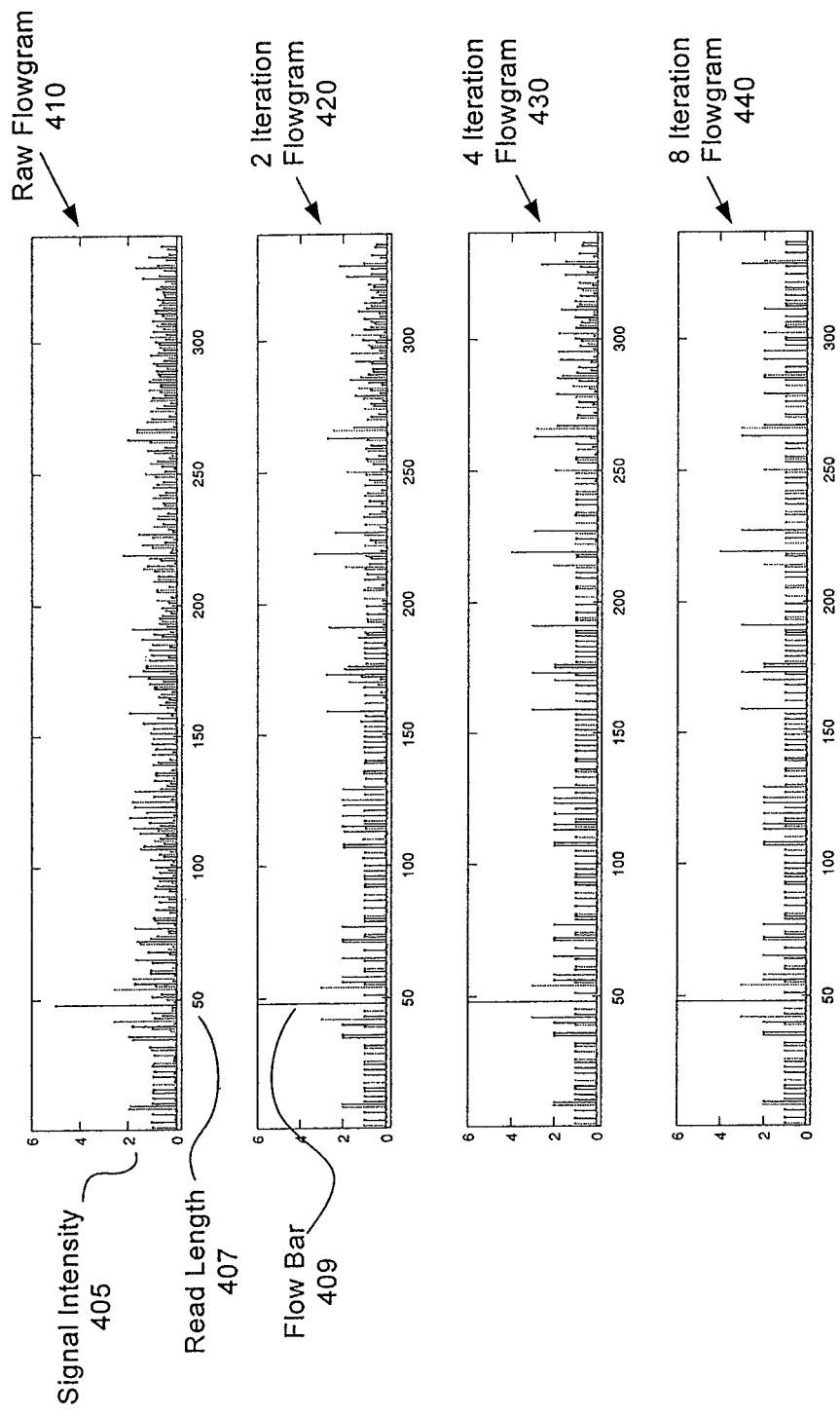

Embodiments of the presently described invention are based, at least in part, upon the discovery that a theoretical or "perfect" flowgram can be converted into a real life observed "dirty" flowgram by a mathematical model of IE and CF. The term "flowgram" as used herein generally refers to a representation of sequencing data generated from a sequencing run that may, for instance, include a graph representation of the sequencing data. For example, a perfect or theoretical flowgram represents data from generated from a sequencing run that has no error from the CAFIE mechanisms described above or other types of background error. Along the same lines a dirty or observed flowgram represents data generated from a sequencing run that includes the CAFIE and background error factors. In the present example, some or all of the error factors may be accurately approximated and applied to the perfect flowgram model to provide a representation of real data obtained from an actual sequencing run.

Importantly, the presently described invention is also based, at least in part, upon the discovery that an inversion of the mathematical model described above can serve to approximate a perfect theoretical flowgram from a dirty observed flowgram. Thus, continuing the example from above an approximation of error may be applied to actual sequencing data represented in an observed flowgram resulting in a perfect or substantially perfect theoretical flowgram representation of the actual sequence data with all or substantially all of the error factors removed.

Those of ordinary skill in the related art will appreciate that the accurate removal of error from data provides for a more efficient and accurate interpretation of said data. Thus, for instance, removing error from data generated in a sequencing run results in more accurate production of calls identifying each nucleic acid species in a sequence generated from a sequence run and higher quality sequence information.

Some embodiments of the presently described invention include systems and methods for analyzing data generated from SBS sequencing runs on a sequencing apparatus. Some examples of SBS apparatus and methods may employ what may be referred to as a pyrophosphate based sequencing approach that may, for instance, comprise one or more of a detection device such as a charge coupled device (CCD) camera, a microfluidics chamber, a sample cartridge holder, or a pump and flow valves. Taking the example of pyrophosphate based sequencing, embodiments of an apparatus may use chemiluminescence as the detection method, which for pyrophosphate sequencing produces an inherently low level of background noise. In the present example, the sample cartridge holder for sequencing may include what is referred to as a "picotiterplate" formed from a fiber optics faceplate that is acid-etched to yield hundreds of thousands of very small wells each enabled to hold a population of substantially identical template molecules. In some embodiments, each population of substantially identical template molecule may be disposed upon a solid substrate such as a bead, each of which may be disposed in one of said wells. Continuing with the present example, an apparatus may include a reagent delivery element for providing fluid reagents to the picotiterplate holders, as well as a CCD type detection device enabled to collect photons emitted from each well on the picotiterplate. Further examples of apparatus and methods for performing SBS type sequencing and pyrophosphate sequencing are described in U.S. patent application Ser. Nos. 10/767,779; 11/195,254 both of which are hereby incorporated by reference herein in their entireties for all purposes.

Further, the systems and methods of the presently described embodiments of the invention may include implementation on a computer readable medium stored for execution on a computer system. For example, several embodiments are described in detail below to process and correct error in signals detected using SBS systems and methods implementable on computer systems.

A computer may include any type of computer platform such as a workstation, a personal computer, a server, or any other present or future computer. Computers typically include known components such as a processor, an operating system, system memory, memory storage devices, input-output controllers, input-output devices, and display devices. It will be understood by those of ordinary skill in the relevant art that there are many possible configurations and components of a computer and may also include cache memory, a data backup unit, and many other devices.

Display devices may include display devices that provide visual information, this information typically may be logically and/or physically organized as an array of pixels. An interface controller may also be included that may comprise any of a variety of known or future software programs for providing input and output interfaces. For example, interfaces may include what are generally referred to as "Graphical User Interfaces" (often referred to as GUI's) that provide one or more graphical representations to a user. Interfaces are typically enabled to accept user inputs using means of selection or input known to those of ordinary skill in the related art.

In the same or alternative embodiments, applications on a computer may employ an interface that includes what are referred to as "command line interfaces" (often referred to as CLI's). CLI's typically provide a text based interaction between an application and a user. Typically, command line interfaces present output and receive input as lines of text through display devices. For example, some implementations may include what are referred to as a "shell" such as Unix Shells known to those of ordinary skill in the related art, or Microsoft Windows Powershell that employs object-oriented type programming architectures such as the Microsoft .NET framework.

Those of ordinary skill in the related art will appreciate that interfaces may include one or more GUI's, CLI's or a combination thereof.

A processor may include a commercially available processor such as an Itanium® or Pentium® processor made by Intel Corporation, a SPARC® processor made by Sun Microsystems, an Athalon™ or Opteron™ processor made by AMD corporation, or it may be one of other processors that are or will become available. Some embodiments of a processor may also include what are referred to as Multi-core processors and/or be enabled to employ parallel processing technology in a single or multi-core configuration. For example, a multi-core architecture typically comprises two or more processor "execution cores". In the present example each execution core may perform as an independent processor that enables parallel execution of multiple threads. In addition, those of ordinary skill in the related will appreciate that a processor may be configured in what is generally referred to as 32 or 64 bit architectures, or other architectural configurations now known or that may be developed in the future.

A processor typically executes an operating system, which may be, for example, a Windows®-type operating system (such as Windows® XP or Windows Vista®) from the Microsoft Corporation; the Mac OS X operating system from Apple Computer Corp. (such as 7.5 Mac OS X v10.4 "Tiger" or 7.6 Mac OS X v10.5 "Leopard" operating systems); a Unix® or Linux-type operating system available from many vendors or what is referred to as an open source; another or a future operating system; or some combination thereof. An operating system interfaces with firmware and hardware in a well-known manner, and facilitates the processor in coordinating and executing the functions of various computer programs that may be written in a variety of programming languages. An operating system, typically in cooperation with a processor, coordinates and executes functions of the other components of a computer. An operating system also provides scheduling, input-output control, file and data management, memory management, and communication control and related services, all in accordance with known techniques.

System memory may include any of a variety of known or future memory storage devices. Examples include any commonly available random access memory (RAM), magnetic medium such as a resident hard disk or tape, an optical medium such as a read and write compact disc, or other memory storage device. Memory storage devices may include any of a variety of known or future devices, including a compact disk drive, a tape drive, a removable hard disk drive, USB or flash drive, or a diskette drive. Such types of memory storage devices typically read from, and/or write to, a program storage medium (not shown) such as, respectively, a compact disk, magnetic tape, removable hard disk, USB or flash drive, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with memory storage device.

In some embodiments, a computer program product is described comprising a computer usable medium having control logic (computer software program, including program code) stored therein. The control logic, when executed by a processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers could include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers could include controllers for any of a variety of known display devices for presenting information to a user, whether a human or a machine, whether local or remote. In the presently described embodiment, the functional elements of a computer communicate with each other via a system bus. Some embodiments of a computer may communicate with some functional elements using network or other types of remote communications.

As will be evident to those skilled in the relevant art, an instrument control and/or a data processing application, if implemented in software, may be loaded into and executed from system memory and/or a memory storage device. All or portions of the instrument control and/or data processing applications may also reside in a read-only memory or similar device of the memory storage device, such devices not requiring that the instrument control and/or data processing applications first be loaded through input-output controllers. It will be understood by those skilled in the relevant art that the instrument control and/or data processing applications, or portions of it, may be loaded by a processor in a known manner into system memory, or cache memory, or both, as advantageous for execution.

Also a computer may include one or more library files, experiment data files, and an internet client stored in system memory. For example, experiment data could include data related to one or more experiments or assays such as detected signal values, or other values associated with one or more SBS experiments or processes. Additionally, an internet client may include an application enabled to accesses a remote service on another computer using a network and may for instance comprise what are generally referred to as "Web Browsers". In the present example some commonly employed web browsers include Netscape® 8.1.2 available from Netscape Communications Corp., Microsoft® Internet Explorer 7 available from Microsoft Corporation, Mozilla Firefox® 2 from the Mozilla Corporation, Safari 1.2 from Apple Computer Corp., or other type of web browser currently known in the art or to be developed in the future. Also, in the same or other embodiments an internet client may include, or could be an element of, specialized software applications enabled to access remote information via a network such as a data processing application for SBS applications.

A network may include one or more of the many various types of networks well known to those of ordinary skill in the art. For example, a network may include a local or wide area network that employs what is commonly referred to as a TCP/IP protocol suite to communicate. A network may include a network comprising a worldwide system of interconnected computer networks that is commonly referred to as the internet, or could also include various intranet architectures. Those of ordinary skill in the related arts will also appreciate that some users in networked environments may prefer to employ what are generally referred to as "firewalls" (also sometimes referred to as Packet Filters, or Border Protection Devices) to control information traffic to and from hardware and/or software systems. For example, firewalls may comprise hardware or software elements or some combination thereof and are typically designed to enforce security policies put in place by users, such as for instance network administrators, etc.

Examples of SBS embodiments typically employ serial or iterative cycles of nucleotide species addition to the template molecules described above. These cycles are also referred to herein as "flows". For example, in each flow either one of the four nucleotide species, A, G, C or T is presented (e.g., for pyrophosphate (PPi) sequencing methods), or all four nucleotide species together are presented to the template-polymerase complex (e.g., for sequencing methods which use a different label associated with each nucleotide specie). Continuing with the present example, a flow may include a nucleotide specie complementary to the nucleotide specie in the template molecule at the sequence position immediately adjacent to the 3' end of the nascent molecule being synthesized, where the nucleotide specie will be incorporated into the nascent molecule. In the present example, the incorporation of the nucleotide specie may be detected in the form of a light signal (e.g. a light signal that may for instance include light generated from a luminescent or fluorescent process) or other signal, such as a mass tag. After each iteration of a flow of a nucleotide specie, a wash method is implemented to remove the unincorporated excess of the nucleotide specie and reagents. Upon completion of the washing stage, the next iteration of a flow presents another nucleotide specie, or mix of nucleotide species, to the template-polymerase complex. In some embodiments a "flow cycle" may refer the addition of four nucleotide species either iteratively or in parallel where for instance one flow cycle includes the addition of all four nucleotide species.

When charted on a flowgram, a value for the detected light or other signal for each flow may be about zero (indicating a nucleotide specie in the flow was not complementary to the nucleotide specie in the template at the next sequence position and thus not incorporated), or about one (indicating incorporation of exactly one nucleotide specie complementary to the nucleotide specie in the template was detected), or about an integer greater than one (indicating incorporation of 2 or more copies of the nucleotide specie presented in the flow complementary two consecutive nucleotide specie in the template were detected).

As described above, a theoretical outcome for an iterative series of flows results in a signal from each flow that should be either exactly zero, or an integer and represented in a perfect flowgram. Through various experimental variations that include CF and IE mechanisms, the actual detected signals tend to fluctuate around these expected theoretical values by varying amounts. The detected signals that include this variation are represented as a dirty or observed flowgram.

The terms flowgram and pyrogram are used interchangeably herein. The terms "perfect flowgram", "clean flowgram" and "theoretical flowgram" are used interchangeably herein. The terms "dirty flowgram", "real-life flowgram" and "observed flowgram" are used interchangeably herein.

Further, as used herein, a "read" generally refers to the entire sequence data obtained from a single nucleic acid template molecule or a population of a plurality of substantially identical copies of the template molecule. A "nascent molecule" generally refers to a DNA strand which is being extended by the template-dependent DNA polymerase by incorporation of nucleotide species which are complementary to the corresponding nucleotide species in the template molecule. The term "completion efficiency" as used herein generally refers to the percentage of nascent molecules that are properly extended during a given flow. The term "incomplete extension rate" as used herein generally refers to the ratio of the number of nascent molecules that fail to be properly extended over the number of all nascent molecules.

Some embodiments of the presently described invention correct the detected signals of each flow to account for the CF and IE mechanisms described above. For example, one aspect of the invention includes calculating the extent of phasic synchronism loss for any known sequence, assuming given levels of CF and IE.

Table 1, illustrated below, provides an example of mathematically modeled threshold values for IE and CF that provide an accuracy of 99% or better (e.g. the read is at least 99% representative of actual sequence of template molecule) for different read lengths. The predicted values presented in Table 1 illustrate the impact of CF and IE effects on sequencing accuracy for various read lengths and the extent of IE and CF error that can be tolerated to achieve a read accuracy of approximately 99%. Table 1 shows that for an uncorrected read a CF rate of no greater than 1% is permissible (assuming IE equals zero for that population) in order for a read length of about 100 sequence positions to be 99% accurate (i.e. completion efficiency of 99% or higher). Furthermore, an IE rate of no greater than 0.25% is permissible (assuming the CF rate equals zero) in order for a read length of about 100 sequence positions to be 99% accurate.

TABLE 1

Predicted rates of error resulting in 99% accuracy at different read lengths

| | Read Length (bases) | | | | | |
|---|---|---|---|---|---|---|
| | 100 | | 200 | | 400 | |
| Incomplete Extension | 0.0 | 0.0025 | 0.0 | 0.0013 | 0.0 | 0.0007 |
| Carry Forward | 0.01 | 0.0 | 0.005 | 0.0 | 0.003 | 0.00 |
| Predicted Accuracy | ~99% | ~99% | ~99% | ~99% | ~99% | ~99% |

It will be understood that the values presented in Table 1 are for the purposes of illustration only and should not be considered limiting. Those of ordinary skill will appreciate that several factors may contribute to variability of values such as the genomic or reference sequences and other parameters used to formulate predictions. For example, typical embodiments of SBS methods generally achieve CF rates that range from 1-2%, while IE rates range from 0.1-0.4% (i.e. completion efficiency ranges from 99.6-99.9%). As described above, correction of CF and IE is desirable because the loss of phasic synchronism has a cumulative effect over the read length and degrades the quality of a read as read length increases.

In one embodiment of the presently described invention, values representing both CF and IE are assumed to be substantially constant across the entire read of a substantially identical template molecule population, such as for instance a population of template molecules residing within a single well of a picotiterplate system. This permits numerical correction of each sequence position across the entire read using two simple parameters "incomplete extension" and "carry forward" without any a priori knowledge of the actual sequence of the template molecule. The system and methods of the presently described embodiments of the invention are useful in determining, and correcting for, the amounts of CF and IE occurring in a population of template molecules. For example, embodiments of the invention correct the signal value detected from each flow for each population of substantially identical template molecules residing in each well to account for CF and IE.

Embodiments of the present invention model the lack of phasic synchronism as a nonlinear mapping:

$$M(p,\epsilon,\lambda)=q \qquad \text{Equation (1):}$$

Wherein:
M is the CAFIE mapping
p is the hypothetical "perfect" flowgram [as array]
$\lambda$ is the completion efficiency parameter
$\epsilon$ is the carry forward parameter
q is the "dirty" flowgram [as array]

A theoretical "perfect" flowgram can be converted into a real-life "dirty" flowgram by use of the mapping model formula given in Equation (1) to estimate IE and CF. A model for such a mapping formula can be generated by, for example, analyzing the errors that are introduced to an observed flowgram (q) by sequencing a polynucleotide template molecule having a known sequence. An illustrative example of the mathematical model given by Equation (1) is illustrated in FIG. 1.

For example on the left hand side of FIG. 1, theoretical flowgram 101 is an illustrative representation of a theoretical (perfect or ideal) flowgram (p), that shows an idealized signal strength value depicted in brackets next to its associated nucleotide specie. Each idealized value of theoretical flowgram 101 is an integer or zero. In the present example, a value of "1" represents a 100% detected signal strength elicited by a single nucleotide incorporation, and "0" represents 0% signal (e.g., in a well comprising a population of 1 million substantially identical template molecules and 1 million nascent molecules, "1" represents the signal elicited when every nascent molecule is extended by a single nucleotide, "2" represents the signal elicited when every nascent molecule is extended by two nucleotides, etc.).

On the right hand side of FIG. 1, observed flowgram 103 is an illustrative representation of a detected signal strength value from an observed (or simulated dirty) flowgram (q). Similarly, each signal strength value in flowgram 103 is depicted in brackets next to its associated nucleotide specie. Also on the right hand side of FIG. 1 is flow 105 that provides a representative number representing the iterative flow sequence associated with a nucleotide specie and signal values (e.g. each iteration of flow 105 represents an addition of a nucleotide specie followed by a wash process). For instance, flow 1 as illustrated in FIG. 1 is associated with the "C" nucleotide specie introduced in said iteration of flow 105 and a corresponds to a signal value for both theoretical flowgram 101 and observed flowgram 103.

In the example of FIG. 1 the differences in signal strength values between theoretical flowgram 101 and observed flowgram 103 for the each flow 105 iteration is indicative, at least in part, of a loss of phasic synchronicity. For instance, the signal values represented in observed flowgram 103 are not integers, rather each are typically slightly higher or slightly lower than ideal value represented in theoretical flowgram 101 for the same iteration of flow 105.

Mapping model 110 represented as "M", may be estimated using known values for parameters 113. For example, parameters 113 include a $\epsilon$ (carry-forward) parameter and a $\lambda$ (completion efficiency) parameter. Parameters 113 may be employed to estimate mapping model 110 and convert the signal values of the theoretical flowgram (p) 101 into the observed values (q) 103. In the present example, the error value represented by mapping model 110 accumulates with each iteration of flow 105, and grows exponentially.

Continuing the example from above, the error represented by the error value may in theory grow exponentially with each flow. For instance, the phasicaly synchronized sequencing reactions associated with each population of substantially identical template molecules become three different phasicaly synchronized sub-populations after a flow iteration. The sub-populations include: a first sub-population of phasicaly synchronized reactions where the nucleotide specie in the flow is properly incorporated at the appropriate sequence position relative to the template molecules (e.g. no CAFIE effects); a second sub-population of phasicaly synchronized reactions where improper incorporation from CF mechanisms has occurred and the reactions are ahead of the sequence position relative of the first population; and a third sub-population of phasicaly synchronized reactions where improper incorporation from IE mechanisms has occurred and the reactions are behind the sequence position of the first population. In the present example, at the next flow iteration three sub-sub-populations will form from each of the three sub-populations described above, and so on. Those of ordinary skill in the related art will appreciate that at an n-th flow iteration, there will be $3^n$ populations of phasicaly synchronized reactions each contributing a signal at flow n.

Further continuing the example from above, FIG. 2 provides an illustrative representation of an inversion of mapping model 110 that is represented in FIG. 2 as inversion mapping model 210. For instance, by estimating the correct values for parameters 113 (e.g. a value for both the $\epsilon$ (carry-forward) and $\lambda$ (completion efficiency) parameters), the signal values of observed flowgram (q) 103 are inverted back to give the signal values of the theoretical flowgram (p) 101.

Those of ordinary skill in the related art will appreciate that the signal values represented in FIGS. 1 and 2 are provided for the purposes of illustration only and that a broad range of signal values are possible. Thus they should not be considered as limiting.

Some embodiments of the invention execute the inverted mapping in two consecutive stages, (i) and (ii) outlined below:
For each nucleotide specie flow i:
(i)—extension of nascent molecule through nucleotide specie addition:

$$\begin{cases} q_i = \lambda \sum_j m_j p_j \\ (m_j, m_{j'}) \leftarrow (m_j, m_{j'}) + \lambda(-1, 1)m_j p_j \end{cases}$$

for all $j$ such that $N_j = N_i$ and $p_j > 0$ (ii)—extension of nascent molecule through nucleotide specie leftover from a previous addition:

$$\begin{cases} q_i \leftarrow q_j + \varepsilon \sum_j m_j p_j \\ (m_j, m_{j'}) \leftarrow (m_j, m_{j'}) + \varepsilon(-1, 1)m_j p_j \end{cases}$$

for all $j$ such that $N_j = N_{i-1}$ and $p_j > 0$

Wherein:
$p_i$ is the theoretical (clean) flowgram signal value at i-th nucleotide specie flow
$q_i$ is the observed (dirty) flowgram signal value at i-th nucleotide specie flow
$m_i$ is the fraction of nucleotide specie molecules available for incorporation at a flowgram sequence position for the i-th nucleotide specie flow
$N_i$ is the i-th nucleotide specie addition (A, C, G, or T)
(j, j') are pair indices such that $p_{j'}$ is the next positive value of $p_j$ on the flowgram The mapping model carries out these calculations flow-by-flow (e.g. iterations of flow 105), and updates observed flowgram (q), and the fraction of the template molecules, m, recursively through stages (i) and (ii).

FIG. 3a provides an illustrative example of models employed for matrix calculations. For example as will be described in greater detail below, forward matrix model 310 may be employed to derive inverse matrix model 320. In the present example, performing matrix calculations using inverse matrix model 320 may be employed to derive estimations for parameters 113. For instance, various values for parameters 113 may be applied in the matrix calculations and evaluated for the degree of fit to observed flowgram 103. Typically, parameters 113 that provide the best fit to observed flowgram (q) 103 are determined to be good estimates for actual values of parameters 113.

Further, FIG. 3b provides an illustrative example of a forward matrix calculation using forward matrix model 310. In the present example, observed flowgram (q) 103 is generated by the matrix calculation using parameters 113 that includes a completion efficiency value $\lambda$=0.95 and a carry forward value $\epsilon$=0.05. Each row associated with an iteration of flow 105 of the matrix records the operations and results of recursive stages (i, ii) for each nucleotide specie flow.

Equation (1) and the recursive stages (i, ii) can be rewritten as a matrix-array operation:

$$[M(p',\epsilon,\lambda)]*p=q \qquad \text{Equation (2):}$$

wherein:
[M(p', $\epsilon$, $\lambda$)] is a matrix
\* is the matrix-array multiplication
p'=sgn(p), is binary encoding of a theoretical or "perfect" flowgram
(e.g., the flowgram p in FIG. 1, p=[0 1 0 2 0 0 1 0 3 0 1 2]$^t$ will be encoded as p'=[0 1 0 1 0 0 1 0 1 0 1 1]$^t$).

The inverse form of Equation (2) gives the inverse mapping, converting the "dirty" observed flowgram (q) 103 back to theoretical flowgram (p) 101:

$$p=[M^{-1}(p',\epsilon,\lambda)]*q \qquad \text{Equation (3):}$$

wherein:
[$M^{-1}$(p',$\epsilon$,$\lambda$)] is the (set-theoretic) inverse matrix An iterative method is used solve the inverse Equation (3), illustrated as inverse matrix model 320 in FIG. 3a, to obtain the theoretical flowgram (p) 101 for each read. This iteration is performed with a given pair of parameters 113 ($\epsilon$, $\lambda$) for the CAFIE inversion:

$$p^{(n+1)}=[M^{-1}(p'^{(n)},\epsilon,\lambda)]*q \qquad \text{Equation (4):}$$

Wherein $p'^{(n)} \equiv sgn(p^{(n)}-threshold)$ and $p^{(1)} \equiv q$ is used as the seed for the calculation. The value of threshold depends on the signal to noise ratios of the system.

Similar to FIG. 3b, FIG. 4a provides an illustrative example of an inverse matrix calculation using inverse matrix model 320. In the present example, theoretical clean flowgram (p) 101 is generated from the observed dirty flowgram (q) 103 using parameters 113 that include on a completion efficiency value lambda=0.95 and a carry forward value epsilon=0.05.

For example, in one implementation a fixed value, threshold=0.2, may be employed. In such an implementation, the binary encoding of a flowgram p' encodes a value "1" when the flowgram value p is greater than 0.2, and encodes a value "0" when the flowgram value p is less than or equal to 0.2. In the present example, the threshold value 0.2 is an estimation of the signal to noise ratio.

Alternatively, some implementations may employ a threshold value in the range between 0 and 1, such as 0.05, 0.1, or 0.3. Thus, the "dirty" observed flowgram (q) 103 can be inverted back to the clean "perfect" theoretical flowgram (p) 101 through Equation (4), for a given pair of parameters 113 ($\epsilon$, $\lambda$). In many implementations, a single iteration of flowgram inversion can generally suffice. In some implementations it may be desirable to perform, 2, 3, or more iterations of flowgram inversion where the accuracy of the flowgram representation may be improved with each iteration, particularly for longer read lengths, until convergence of the calculation on a solution with a desired quality. In a preferred embodiment, 1 iteration, or 2 iterations of flowgram inversion may be performed in the interest of computational efficiency. Also, some embodiments of the invention implemented by computer code may enable a user selection of a number of iterations to perform and/or serially perform each iteration in response to a user selection. For example, a user may perform selections using methods known in the art such as inputting values in one or more fields or selection of buttons presented in a GUI. In the present example, a user may input a value indicating a number of iterations to perform and/or the user may select a button to execute an iteration of the invention. Further, the user may select an indication of data quality where the invention iterates until the level of data quality is achieved.

FIG. 4b provides an illustrative example of how results may be improved in successive numbers of iterations using the method of Equation (4). Raw flowgram 410 illustrates an embodiment of observed flowgram (q) 103 having parameter values 113 that include a completion efficiency value $\lambda$=0.997 and carry-forward value $\epsilon$=0.03 from 336 flow iterations of nucleotide specie addition each iteration represented by flow bar 409. For instance, each flow bar 409 is representative of a flow of a nucleotide specie and each specie may be specifically represented by a color or pattern of bar 409. Further, the detected or corrected signal value associated with each flow is represented by the height of bar 409 relative to the scale given by signal intensity 405.

Those of ordinary skill in the related art will appreciate that there is a high degree of variability in raw flowgram 410 with respect to the value of signal intensity 405 for flow bars 409, particularly for read length greater than 50 sequence positions relative to the scale given by read length 407. In other words, signal values for the majority of flow bars 409 do not include signal values that are integers. 2 iteration flowgram 420 illustrates the same embodiment of observed flowgram (q) 103 after 2 iterations of correction using an embodiment of the invention. The consistency of signal intensity 405 for flow bars 409 is improved particularly for flow bars 409 at read length 407 position 150 or less. Similarly improvements of data quality are demonstrated in 4 iteration flowgram 430 and 8 iteration flowgram 440 respectively where flowgram 440 illustrates that substantially all flow bars 409 show consistency and integer values.

In some embodiments, estimations of values for parameters 113 may be determined using Equation (4). For example, the best-fitting value for the completion efficiency parameter ($\lambda$) may be determined by performing test calculations using Equation (4) inputting different values for the completion efficiency parameter while using a fixed value for the CF parameter. In the present example, values of $\lambda=1$, 0.999, 0.998, . . . , 0.990, with a fixed CF value $\epsilon=0$ may be successively employed and results for each obtained. In different embodiments, the 0.001 interval between input $\lambda$ values may be replaced by other intervals, such as, for instance, interval values of 0.05, 0.01, 0.005, 0.001, 0.0005, 0.0001, or the like.

Continuing with the present example, if any signal value 405 for a flow bar 409 in a computed theoretical flowgram (p) falls below zero after solving Equation (4) using an input value for $\lambda$, then that $\lambda$ value is declared as the value of the best-fitting completion efficiency parameter. Once the best fitting value of $\lambda$ is determined use of subsequently smaller $\lambda$ values will result in what is referred to as "over-fitting" and produce artificially-negative flow signals. Also in the present example, a corrected signal value 405 for some flow bar 409 at a sequence position after a long series of flow bars 409 representing homopolymers (e.g. a series of sequence positions comprising the same nucleotide species) may fall below zero. This zero-crossing point is illustrated in oval 503 in FIG. 5, and the best-fit completion efficiency is denoted as $\lambda^*$ hereafter.

Likewise, in some embodiments the effect of CF may be addressed by a similar approach. For example, values for the CF parameter may be tested that, for instance, may include values of $\epsilon=0$, 0.0025, 0.005, 0.0075, 0.01, . . . , 0.04 with the completion efficiency parameter $\lambda$ fixed at the previously found value $\lambda^*$. This is illustrated in FIG. 5, as step 2→3, where oval 503 indicates the starting position 2 ($\epsilon$, $\lambda$)=(0, $\lambda^*$). In the present example, the 0.0025 interval between input values for $\epsilon$ is presented for the purpose of illustration and can be replaced by other small interval values such as, for instance, interval values of 0.05, 0.01, 0.005, 0.001, 0.0005, 0.0001, 0.00001, or the like. If any signal value 405 for a flow bar 409 in a computed theoretical flowgram (p) falls below zero after solving Equation (4) using an input value for $\epsilon$ (e.g., any signal value 405 for a flow bar 409 other than the signal value 405 for flow bars 409 that fell below zero during the search along the $\lambda$ path), then that $\epsilon$ value is declared as the value of the best-fitting CF parameter. Once the best fitting value of $\epsilon$ is determined use of subsequently larger values will result in over-fitting and produce artificially negative flow signals. Also in the present example, a corrected signal value 405 for some flow bar 409 at a sequence position before a long series of flow bars 409 representing homopolymers may fall below zero. This zero-crossing point is illustrated in oval 505 in FIG. 5, and the best-fit CF is denoted as $\epsilon^*$ hereafter.

FIG. 5 provides an illustrative example where, for instance, the abscissa represents completion efficiency axis 520, and the ordinate represents CF axis 510. Graphs within ovals 501, 503, and 505 each represent steps as described above and comprise an exemplary portion of a flowgram showing three signals. For instance, the center bar represents the main signal bar 537, flanked by the left minor signal (CF bar 535), and the right minor signal (IE bar 533). Oval 501 illustrates the step of an original observed flowgram (q) 103, where main signal bar 537 is diminished by phasic asynchronism, and the minor signals of CF bar 535 and IE bar 533 represent noise caused by phasic asynchronism. Oval 503 represents a step when IE has been corrected, where the signal associated with IE bar 533a is eliminated, and the center main signal bar 537 is increased accordingly. As described above, the point where IE has been corrected may, for instance, include the zero-crossing point for the best-fit completion efficiency parameter and denoted as $\lambda^*$. Oval 505 represents a further step where CF has been corrected illustrated by the elimination of signal associated with CF bar 535a, and the center main signal bar 537 is increased accordingly. As described above, the point where CF has been corrected may, for instance, include the zero-crossing point for the best-fit completion efficiency parameter and denoted as $\epsilon^*$. Oval 505 illustrates the result of correction which is an approximation of the theoretical, expected flowgram from which noise attributable to phasic asynchronism errors has been substantially removed.

Thus, since the amounts of CF and IE, as well as the underlying template molecule sequence p, are unknown a priori, the methods of the invention can be used in a complete de-novo analysis mode. No prior knowledge of the polymerase incorporation efficiency (i.e. $\lambda$) or the effectiveness of the nucleotide wash-out (i.e. $\epsilon$) is necessary; nor are any reference nucleotide sequences required to perform the inversion.

In some embodiments, the search process for parameter estimation described above constructs a matrix [M] through stages (i, ii) at every input search interval of $\epsilon$ and $\lambda$, which is limiting from a computational efficiency perspective. Such limitations may be overcome, at least in part, by employing approximations on the matrix construction operation. For example, one can avoid re-constructing the matrix at every search interval and hence greatly improve the computational speed. Two such methods are described below:

Method 1:

At small values of $\epsilon$ and $(1-\lambda)$ (e.g., $(1-\lambda)<=0.001$ and $\epsilon<=0.0025$), the matrix [M] is decomposed, and approximated into a form:

$$[M(p',\epsilon,\lambda)] \sim [L(p',\Delta\lambda)]^{\phi} * [U(p',\Delta\epsilon)]^{\overline{\omega}} \qquad \text{Equation (5):}$$

wherein:

$\Delta\epsilon=0.0025$ and $\Delta\lambda=0.001$, are the intervals in the $\epsilon$- and $\lambda$-axis, respectively.

$\phi$ and $\overline{\omega}$ are the matrix powers, with the properties of $\overline{\omega} \sim \epsilon/\Delta\epsilon$ and $\phi \sim (1-\lambda)/\Delta\lambda$.

[L(p', $\Delta\lambda$)] is a lower diagonal matrix, which models the effect of IE at a small deficiency $\Delta\lambda$.

[U(p', $\Delta\lambda$)] is an upper diagonal matrix, which models the effect of CF at small deficiency $\Delta\epsilon$.

Through this decomposition, Equation (5) constructs the lower diagonal matrix L and upper diagonal matrix U only once along the search path, and the degrees of incompletion and carry-forward at the search grid, ($\epsilon$, $\lambda$), are modeled by the powers of the matrices, ($\bar{\omega}$, $\phi$). The small values in the search intervals, $\Delta\epsilon$=0.0025 and $\Delta\lambda$=0.001, may be replaced by other small values, such as, for example, 0.05, 0.01, 0.005, 0.001, 0.0005, 0.0001, or the like.

Instead of searching on ($\epsilon$, $\lambda$)-grids previously exhibited, the method here stages through a set of ($\bar{\omega}$, $\phi$)-grids, which are preferably positive integers to facilitate the computations of matrix powers. The best-fit ($\bar{\omega}^*$, $\phi^*$) are defined at the zero-crossing condition; the corresponding completion efficiency and CF parameters are $\lambda^*=(1-\phi^*\Delta\lambda)$ and $\epsilon^*=\bar{\omega}^*\Delta\epsilon$.
Method 2:
Following Equation (5) at small $\epsilon$ and $(1-\lambda)$ cases, the lower and upper diagonal power matrices, $[L]^\phi$ and $[U]^{\bar{\omega}}$, are further approximated by $$[L]^\phi \equiv ([I]+[l])^\phi \sim [I]+\phi[l] \quad \text{Equation (6):}$$

$$[U]^{\bar{\omega}} \equiv ([I]+[u])^{\bar{\omega}} \sim [I]+\bar{\omega}[u] \quad \text{Equation (7):}$$

wherein:
[I] is the identity matrix.
[l] and [u] are off-diagonal matrices of [L] and [U], respectively.

This formulates a by-pass of the stage of computing matrix powers, and hence provides further speed up (e.g. decrease in) in the computing time. The search space in $\bar{\omega}$, $\phi$) now contains all positive real numbers. The best-fit ($\bar{\omega}^*$, $\phi^*$) are defined at the zero-crossing condition; the corresponding completion efficiency and CF parameters are $\lambda^*=(1-\phi^*\Delta\lambda)$ and $\epsilon^*=\bar{\omega}^*\Delta\epsilon$.

The embodiments presented here are based on constructing and inversing the matrices, and a two-dimensional search in the ($\epsilon$, $\lambda$) plane to probe the optimal pair of CAFIE parameters. These calculations are done on each population of substantially identical template molecules, which for example may include a well-by-well analysis in a picotiterplate type system. In some embodiments, a matrix is constructed for each population/well to produce optimal CAFIE values ($\epsilon^*$, $\lambda^*$). FIG. 6 provides an illustrative example of the distribution of completion efficiency parameter 605 values $\lambda^*$ and CF parameter 607 values $\epsilon^*$ in a sample of several hundred thousand populations/wells 603, as calculated by use of the inversion/search Method 1 described above. Calculation by use of the above-described Method 2, which requires less computational time than Method 1, provides similar results.

The embodiments described above also assume that the rates associated with the constant completion efficiency $\lambda$ and CF $\epsilon$ parameters remain constant throughout the sequencing runs. This assumption can be alleviated by applying the CAFIE search and the inversion procedures on what may be referred to as "flow windows" in flowgrams that comprise several flow cycles (wherein "several" means any integer between 1 and the total number of flow cycles). For example, each flow window is a subset of the full set of flow cycles represented in a flowgram, with a pair of CAFIE parameters and a corresponding clean theoretical flowgram 101 needing to be found. In the present example, each flow window is arranged such that it starts from the first flow in the flowgram associated with a sequencing run and ends at a certain flow shorter or equal to the full length of the flow cycles in the flowgram, where each smaller flow window is nested within a larger one. For each flow window n, the search and inversion processes occur independently to produce a set of CAFIE parameters 113, which are now functions of window indices n: $\epsilon^*=\epsilon^*(n)$ and $\lambda^*=\lambda^*(n)$. The computed clean theoretical flowgram 101, p(n), also nested, is the result of these variable values of the CAFIE parameters depending on the indices n. A "stitching" process: p=p(n) for flows between windows (n−1) and n, re-assembles the flow window sequences p(n) into the final clean flowgram (p) 101.

In the same or alternative embodiments, the assumption of constant values for $\lambda$ and $\epsilon$ may be eliminated by another method. For example, completion efficiency $\lambda$ and CF $\epsilon$ parameters can assume parametric forms, such as exponentials, for each nucleotide specie addition "N" ("A", "G", "C", or "T"), and as functions of flow position "f" (1, 2, 3, ...):

$$\lambda_N(f)=\lambda^0_N * \exp(-\delta_N * f),$$

$$\epsilon_N(f)=\epsilon^0_N * \exp(-\beta_N * f).$$

Wherein:
$\lambda_N(f)$ is the completion efficiency of nucleotide specie "N" at "f"-th flow
$\epsilon_N(f)$ is the CF of nucleotide specie "N" at "f"-th flow
$\lambda^0_N$ and $\epsilon^0_N$ are the initial values
$\delta_N$ and $\beta_N$ are the attenuation rates
Search methods are applied in the four parameter spaces, $\lambda_N(0)$, $\epsilon_N(0)$, $\delta_N$ and $\beta_N$, to determine the optimal values.

In addition, those of ordinary skill in the related art will also appreciate that other sources of noise not related to the described CAFIE mechanisms may exist. Such sources of noise may include, but are not limited to electronic sources such as what may be referred to as "Dark Current", optical sources, biological sources, chemical sources, or other sources known in the art or that may be discovered in the future. Some embodiments of the presently described invention may exhibit varying levels of sensitivity to the other sources of noise that may, in many applications, be at a substantially consistent and/or predictable level. For example, predictable and consistent levels of noise attributable to known or unknown sources are generally easy to correct. One method of correction is to mathematically add or subtract a value associated with the noise (depending upon whether the noise adds excess signal or reduces detected signal) from all signal values associated with a flow.

In some embodiments where the level of noise is not predictable, at least in part, estimations of the level of noise may be derived from information embedded in the signal data. For example, for nucleotide species known or predicted to not be present at a sequence position it is expected that the actual signal value should equal to zero. Therefore, any detected signal may be attributable to all sources of noise in the system. In the present example, since the presently described invention estimates noise form CAFIE mechanisms such noise may be removed from the data and the underlying noise revealed. In the present example, the estimates may be improved by looking at all "zero-mer" sequence positions in a sequence run. In this case, the value of "threshold" in the binary encoding p' Equation (4), can be dynamically determined for each run, to represent its noise level, instead of a fixed value as described in the previous embodiment above.

Even further, some embodiments of the present invention may include what may be referred to as "safety criteria" to prevent over correction of the sequence data represented in an observed flowgram. As described above, over correction can cause an exponential accumulation in error introduced as the described algorithm iterates. For example, the other sources of noise described above may determine the safety criteria that include an amount of correction to be applied to the signal data. For example, some implementations may assume a given level of noise from other non-CAFIE sources and apply a safety criteria of what may be referred to as 60% correction (e.g. 100% implies full correction) to the data. This estimate uses a "hybrid" flowgram, "0.6p+0.4q", comprising 60% of the computed clean flowgram p and 40% of the observed dirty flowgram q. Alternatively, if the non-CAFIE noise is at a "low" level a higher percentage of correction may be applied, such as for instance 80%.

EXAMPLE 1

Figure 7:
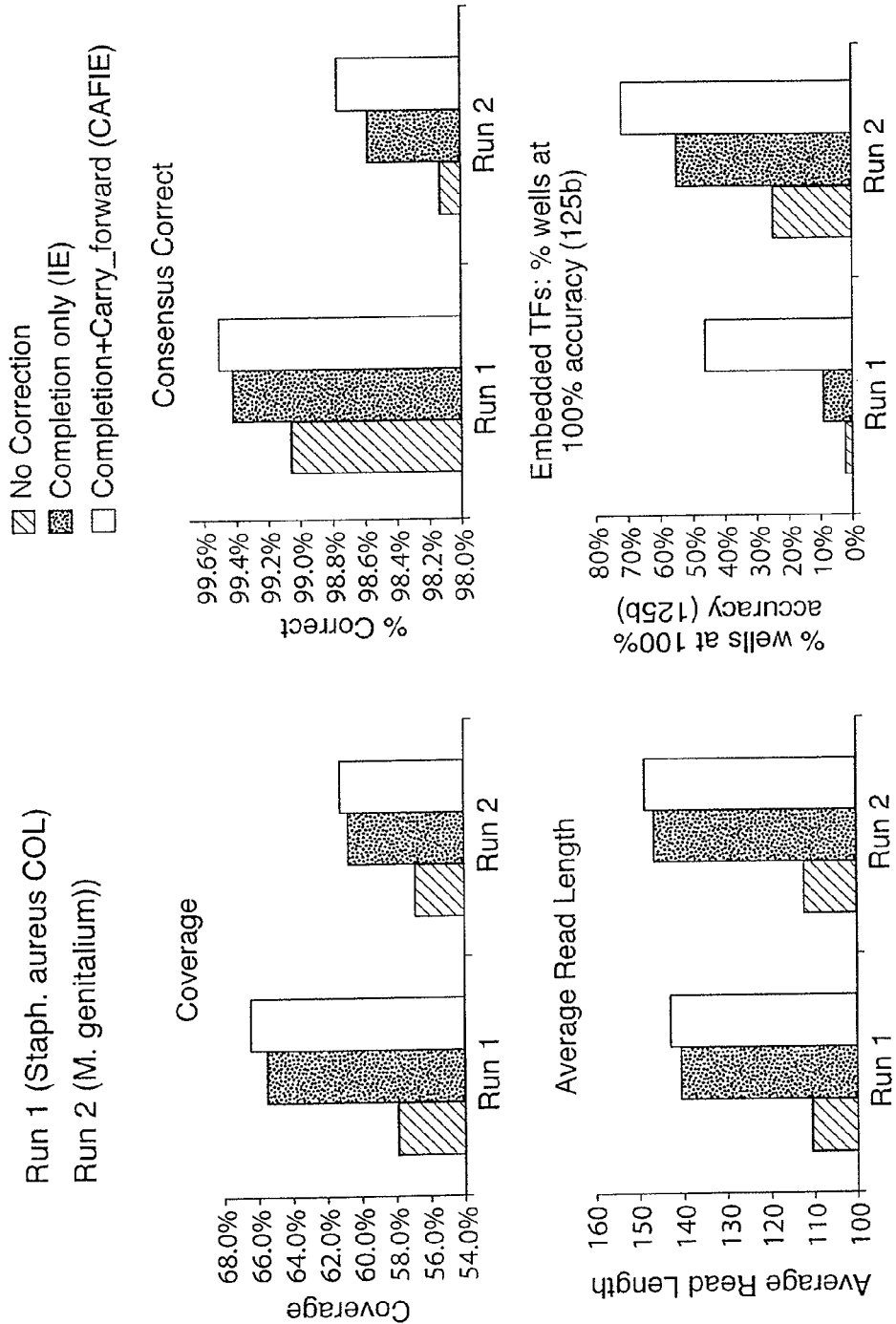
FIG. 7 is a simplified graphical representation of one embodiment of the effects of IE correction only, and the effects of CAFIE correction.

The genomes of Staphylococcus aureus COL and Mycoplasma genitalium were shotgun sequenced on a 454 Life Sciences Genome Sequencer (Margulies et al., 2005, incorporated by reference above). FIG. 7 provides an illustrative example of the effects of IE correction only and CAFIE correction on genome coverage, correctness of the consensus sequence, medium read length, and percentage of wells having achieved 100% accuracy of read lengths of over 125 sequence positions. By each of these measures, CAFIE correction was superior to IE correction alone. IE correction alone was superior to the results achieved without correction. Beads with control sequences were prepared separately and mixed with the experimental sample prior to preparation of the array.

Through the use of the above procedures the average read length for a 63-cycle run was increased from 112 sequence positions to 147 sequence positions which is near the theoretical maximum for a 63-cycle or 252 flow iterations (e.g. each flow cycle includes 4 nucleotide specie flow iterations). The theoretical maximum is computed by multiplying the number of flow cycles, 63 in this case, by the number of sequence positions (2.5) that are extended, on average, in each cycle of 4-nucleotide additions: 63×2.5=157.5 (theoretical maximum). The 147 sequence position average read length was determined by mapping the flowgrams to a known genome sequence, with 95% accuracy over the flow cycles.

Further, disclosed herein are four exemplary pseudo-code computer programs implementable by a data processing application as described above using the above-described Method 1, namely:
(1) buildTransitionMatrixIEOnly.c
  Builds transition matrix for Incomplete Extension
(2) buildTransitionMatrixCFOnly.c
  Builds transition matrix for Carry Forward
(3) cafieCorrectOneNukeTraceFastTMC2.c
  Inverts transition matrix computed in (1), and searches for IE value
(4) cafieCorrectOneNukeTraceFastCarryForwardOnly.c
  Inverts transition matrix computed in (2), and searches for CF value The input is the dirty flowgram and the flow order (nucleotide addition) for each read; the output is the cleaned flowgram and the optimal values ($\delta^*$, $\lambda^*$). It will be understood that these pseudo-code computer programs are only illustrative and various modifications and variations are within the scope of the present invention.

Thus it is seen that methods and systems are provided for correcting errors in sequence data obtained during the sequencing of nucleic acids. Although particular embodiments have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the invention as defined by the claims. Other aspects, advantages, and modifications are considered to be within the scope of the following claims. The claims presented are representative of the inventions disclosed herein. Other unclaimed inventions are also contemplated. The right to pursue such inventions in later claims is hereby reserved.

What is claimed is:

1. A method for correcting phasic synchrony error in sequence data captured from a population of substantially identical copies of a template nucleic acid, comprising the steps of:
  generating a plurality of signal values each detected in response to an incorporation of a nucleotide species in a sequencing reaction with the population of substantially identical copies of a template nucleic acid;
  estimating a carry forward parameter and an incomplete extension parameter using a plurality of binary values encoding of a sequence of the template nucleic acid, wherein the carry forward parameter comprises a numerical value representing a measure of one or more of the substantially identical copies of the template nucleic acid ahead of an extension phase of the population, and the incomplete extension parameter comprises a numerical value representing a measure of one or more of the substantially identical copies of the template nucleic acid behind the extension phase of the population; and
  correcting the signal values for phasic synchrony error using the carry forward parameter and the incomplete extension parameter.

2. The method of claim 1, wherein:
the binary values comprise an integer value representing the incorporation of the nucleotide species.

3. The method of claim 1, wherein:
the binary values comprise an integer value of 0 or 1.

4. The method of claim 1, wherein:
the step of estimating further comprises using the plurality of signal values each corresponding to one of the binary values.

5. The method of claim 1, wherein:
the binary values each comprise an idealized signal strength value for each position of the sequence of the template nucleic acid.

6. The method of claim 1, wherein:
the binary values are generated from the signal values using a threshold value.

7. The method of claim 6, wherein:
the threshold value comprises a number in the range from 0 to 1.

8. The method of claim 7, wherein:
the threshold value comprises a 0.2 value.

9. The method of claim 7, wherein:
the threshold value comprises a 0.3 value.

10. The method of claim 7, wherein:
the threshold value is dynamically determined using the signal value associated with a introduction of one or more nucleotide species at one or more of the positions of known composition.

11. The method of claim 10, wherein:
the known composition comprises a different nucleotide species than the introduced nucleotide species, wherein an expected signal value is equal to zero.

12. A system for correcting phasic synchrony error in sequence data captured from a population of substantially identical copies of a template nucleic acid, comprising:
a computer comprising program code stored for execution thereon, the program code performing a method comprising the steps of:
generating a plurality of signal values each detected in response to an incorporation of a nucleotide species in a sequencing reaction with the population of substantially identical copies of a template nucleic acid;
estimating a carry forward parameter and an incomplete extension parameter using a plurality of binary values encoding of a sequence of the template nucleic acid, wherein the carry forward parameter comprises a numerical value representing a measure of one or more of the substantially identical copies of the template nucleic acid ahead of an extension phase of the population, and the incomplete extension parameter comprises a numerical value representing a measure of one or more of the substantially identical copies of the template nucleic acid behind the extension phase of the population; and
correcting the signal values for phasic synchrony error using the carry forward parameter and the incomplete extension parameter.

13. The system of claim 12, wherein:
the binary values comprise an integer value representing the incorporation of the nucleotide species.

14. The system of claim 13, wherein:
the binary values comprise an integer value of 0 or 1.

15. The system of claim 12, wherein:
the step of estimating further comprises using the plurality of signal values each corresponding to one of the binary values.

16. The system of claim 12, wherein:
the binary values each comprise an idealized signal strength value for each position of the sequence of the template nucleic acid.

17. The system of claim 12, wherein:
the binary values are generated from the signal values using a threshold value.

18. The system of claim 17, wherein:
the threshold value comprises a number in the range from 0 to 1.

19. The system of claim 18, wherein:
the threshold value comprises a 0.2 value.

20. The system of claim 18, wherein:
the threshold value comprises a 0.3 value.

21. The system of claim 18, wherein:
the threshold value is dynamically determined using the signal value associated with a introduction of one or more nucleotide species at one or more of the positions of known composition.

22. The system of claim 21, wherein:
the known composition comprises a different nucleotide species than the introduced nucleotide species, wherein an expected signal value is equal to zero.

* * * * *

UNITED STATES PATENT AND TRADEMARK OFFICE
CERTIFICATE OF CORRECTION

PATENT NO.       : 9,587,274 B2
APPLICATION NO.  : 13/608841
DATED            : March 7, 2017
INVENTOR(S)      : Yi-Ju Chen et al.

Page 1 of 1

It is certified that error appears in the above-identified patent and that said Letters Patent is hereby corrected as shown below:

On the Title Page

Item (63), Related U.S. Application Data:
"Continuation of application No. 12/224,065, filed as application No. PCT/US2007/004187 on February 15, 2007, now Pat. No. 8,301,394."

Should read:
-- Continuation of application No. 12/224,065, now Pat. No. 8,301,394, which is a National Stage of International application No. PCT/US2007/004187, filed on February 15, 2007. --

Item (56), References Cited, Other Publications:
"Margulies et al. "Genome Sequencipkg in Microfabriated High-Density Picolitre Reactors." *Nature*. 437 (2005):376-380, pp. 376-380."

Should read:
-- Margulies et al. "Genome Sequencing in Microfabricated High-Density Picolitre Reactors." *Nature*. 437 (2005):376-380, pp. 376-380. --

Signed and Sealed this
Thirtieth Day of May, 2017

Michelle K. Lee
*Director of the United States Patent and Trademark Office*